(12) United States Patent
Tkaczyk et al.

(10) Patent No.: US 7,870,006 B2
(45) Date of Patent: Jan. 11, 2011

(54) METHODS AND SYSTEMS FOR MANAGING CLINICAL RESEARCH INFORMATION

(75) Inventors: John Eric Tkaczyk, Delanson, NY (US); Maria Iatrou, Clifton Park, NY (US); Naresh Kesavan Rao, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 3153 days.

(21) Appl. No.: 10/065,159

(22) Filed: Sep. 23, 2002

(65) Prior Publication Data

US 2004/0059597 A1  Mar. 25, 2004

(51) Int. Cl.
G06Q 50/00 (2006.01)
G06F 19/00 (2006.01)

(52) U.S. Cl. ............................................. 705/2; 705/3

(58) Field of Classification Search ................. 705/2–3
See application file for complete search history.

(56) References Cited

U.S. PATENT DOCUMENTS

| | | | |
|---|---|---|---|
| 4,737,921 A * | 4/1988 | Goldwasser et al. | 345/421 |
| 5,666,953 A | 9/1997 | Wilk | |
| 5,715,823 A | 2/1998 | Wood et al. | |
| 5,793,933 A | 8/1998 | Iwamasa | |
| 5,805,796 A | 9/1998 | Finch et al. | |
| 5,890,129 A | 3/1999 | Spurgeon | |
| 5,903,889 A | 5/1999 | de la Huerga et al. | |
| 5,935,060 A | 8/1999 | Iliff | |
| 5,960,085 A | 9/1999 | de la Huerga | |
| 5,991,731 A * | 11/1999 | Colon et al. | 705/3 |
| 6,029,169 A | 2/2000 | Jenkins | |
| 6,196,970 B1 * | 3/2001 | Brown | 600/300 |
| 6,209,004 B1 | 3/2001 | Taylor | |
| 6,272,468 B1 | 8/2001 | Melrose | |
| 6,496,827 B2 * | 12/2002 | Kozam et al. | 707/10 |
| 6,820,235 B1 * | 11/2004 | Bleicher et al. | 715/501.1 |
| 6,839,678 B1 * | 1/2005 | Schmidt et al. | 705/3 |
| 7,054,823 B1 * | 5/2006 | Briegs et al. | 705/2 |
| 2002/0002474 A1 * | 1/2002 | Michelson et al. | 705/3 |

(Continued)

OTHER PUBLICATIONS

Lamb, Kristen A. Bridging the Gap between Drug Discovery and Market. Introduction: The Rise of Contract Research Organizations. Feb. 2, 1998. [Retrieved on Jun. 2, 2003]. Retrieved from Internet. URL: <http://ledalaw.harvard.edu/leda/data/203/klamb.pdf>.*

(Continued)

Primary Examiner—Robert W Morgan
Assistant Examiner—Tran Nguyen
(74) Attorney, Agent, or Firm—Fletcher Yoder, PC

(57) ABSTRACT

A method for managing clinical study (CS) information for a clinical research entity using a server system coupled to a centralized database and at least one client system is provided. The centralized database has a plurality of templates stored therein. The method includes receiving at the server system CS information relating to at least one patient involved in a clinical study wherein the CS information is entered through a user selected template displayed on the client system, storing CS information received at the server system in the centralized database, tracking CS information stored in the centralized database, updating the centralized database periodically with newly received CS information to maintain CS information, and providing CS information in response to an inquiry.

40 Claims, 4 Drawing Sheets

U.S. PATENT DOCUMENTS

| | | | | |
|---|---|---|---|---|
| 2002/0029155 | A1* | 3/2002 | Hetzel et al. | 705/2 |
| 2002/0032581 | A1* | 3/2002 | Reitberg | 705/2 |
| 2002/0035486 | A1* | 3/2002 | Huyn et al. | 705/3 |
| 2002/0038310 | A1* | 3/2002 | Reitberg | 707/104.1 |
| 2002/0042723 | A1* | 4/2002 | Rice et al. | 705/2 |
| 2002/0099570 | A1* | 7/2002 | Knight | 705/2 |
| 2002/0120471 | A1* | 8/2002 | Drazen | 705/3 |
| 2002/0143577 | A1* | 10/2002 | Shiffman et al. | 705/2 |
| 2002/0188475 | A1* | 12/2002 | Banta et al. | 705/3 |
| 2002/0192159 | A1* | 12/2002 | Reitberg | 424/9.1 |
| 2002/0198739 | A1* | 12/2002 | Lau et al. | 705/3 |
| 2003/0229514 | A2* | 12/2003 | Brown | 705/2 |
| 2004/0019259 | A1* | 1/2004 | Brown et al. | 600/300 |

OTHER PUBLICATIONS

Lamb, Kristen A. Bridging the Gap between Drug Discovery and Market. Introduction: The Rise of Contract Research Organizations. Feb. 2, 1998. [Retrieved on Jun. 2, 2003]. Retrieved from Internet. URL:<http://leda.law.harvard..edulled/ldata/2031klamb.pd>.*

* cited by examiner

METHODS AND SYSTEMS FOR MANAGING CLINICAL RESEARCH INFORMATION

BACKGROUND OF INVENTION

This invention relates generally to clinical research and, more particularly, to network-based methods and systems for managing clinical research information.

At least some known clinical research entities conduct clinical studies with selected patients to evaluate the effectiveness of clinical applications and medical equipment utilized in the treatment of these patients. These clinical studies include the collection of a significant amount of data from a plurality of patients including at least one of a patient name, a patient sex, a patient medical history, a patient weight, a patient height, a patient age, a patient ID number, a modality of treatment and/or diagnosis, a type of medical application utilized, medical equipment utilized in treatment and/or diagnosis, treatment and/or diagnosis results, modeled images, x-rays, manufacturing information and documents relating to the medical equipment utilized, engineering information and documents relating to the medical equipment utilized, marketing information and documents, and other documents or information relating to the treatment and/or diagnosis of a patient within a specific clinical study. Historically, such data has been maintained in paper form. For clinical research entities that conduct multiple clinical studies with multiple patients maintaining such data in a manner wherein it may be effectively utilized by a plurality of people can be difficult and costly.

When conducting a clinical study, researchers at a clinical research entity may be required to review a significant amount of data in numerous forms and in numerous locations. The data relates to the patients in the clinical study. Managing this information such that it can be viewed in a standardized form is extremely difficult, time consuming, and costly. Moreover, sharing this information among others, including other researchers, physicians, radiologists, technicians, physicists, technical engineers, and reconstruction engineers, that may be located in a plurality of locations throughout the world, is extremely difficult.

By enabling a clinical research entity to better manage clinical study data, which includes placing it in a standardized format, the clinical study data may be more easily viewed and analyzed by selected persons which facilitates medical diagnoses, optimizes the use of medical equipment in the diagnoses and treatment of patients, and facilitates the production of next generation medical equipment and the optimization of clinical applications.

SUMMARY OF INVENTION

In one aspect, a method for managing clinical study (CS) information for a clinical research entity using a server system coupled to a centralized database and at least one client system is provided. The centralized database has a plurality of templates stored therein. The method includes receiving at the server system CS information relating to at least one patient involved in a clinical study wherein the CS information is entered through a user selected template displayed on the client system, storing CS information received at the server system in the centralized database, tracking CS information stored in the centralized database, updating the centralized database periodically with newly received CS information to maintain CS information, and providing CS information in response to an inquiry.

In another aspect, a method for managing clinical study (CS) information for a clinical research entity using a server system coupled to a centralized database and at least one client system is provided. The at least one client system is in communication with at least one medical device. The centralized database has a plurality of templates stored therein. The method includes using a template selected by a user from the plurality of templates stored in the centralized database to gather protocols for operating the at least one medical device, operating the at least one medical device based on the entered protocols, receiving at the server system CS information that relates to at least one patient involved in a clinical study wherein the CS information is entered through a user selected template displayed on the client system and is generated as part of the operation of the at least one medical device including at least one of x-rays and diagnostic images, storing CS information received at the server system in the centralized database, tracking CS information stored in the centralized database, updating the centralized database periodically with newly received CS information to maintain CS information, providing CS information in response to an inquiry, and transmitting from the server system to the at least one client system at least one report relating to CS information and findings for at least one of a clinical study and a patient involved in a clinical study.

In another aspect, a network based system for managing clinical study (CS) information is provided. The system includes a client system having a browser, a centralized database for storing information and a plurality of templates, and a server system configured to be coupled to the client system and the database. The server system is configured to receive CS information relating to at least one patient involved in a clinical study wherein the CS information is entered through a user selected template displayed on the client system, store CS information in the centralized database, track CS information, update the centralized database periodically with newly received CS information to maintain CS information, and provide CS information in response to an inquiry by a user.

In another aspect, a network based system for managing clinical study (CS) information is provided. The system includes a client system having a browser, at least one medical device in communication with the client system, a centralized database for storing information and a plurality of templates, and a server system configured to be coupled to the client system and the database. The server system is further configured to use a template selected by a user from the plurality of templates stored in the centralized database to gather protocols for operating the at least one medical device, operate the at least one medical device based on the entered protocols, and receive CS information relating to at least one patient involved in a clinical study wherein the CS information is entered through a user selected template displayed on the client system and generated as part of the operation of the at least one medical device including at least one of x-rays and diagnostic images. The server system is further configured to store CS information in the centralized database, track CS information, update the centralized database periodically with newly received CS information to maintain CS information, provide CS information in response to an inquiry, and transmit to the client system at least one report relating to CS and findings for at least one of a clinical study and a patient involved in a clinical study.

In another aspect, a computer program embodied on a computer readable medium for managing clinical study (CS) information is provided. The program includes a code segment that receives CS information relating to at least one patient involved in a clinical study through a user selected template displayed on a client system, maintains a database by adding, deleting and updating CS information, tracks CS information, provides CS information in response to an inquiry by a user, and transmits to the client system at least one report summarizing CS information and findings relating to at least one of a clinical study and a patient involved in a clinical study.

DETAILED DESCRIPTION

Figure 1:
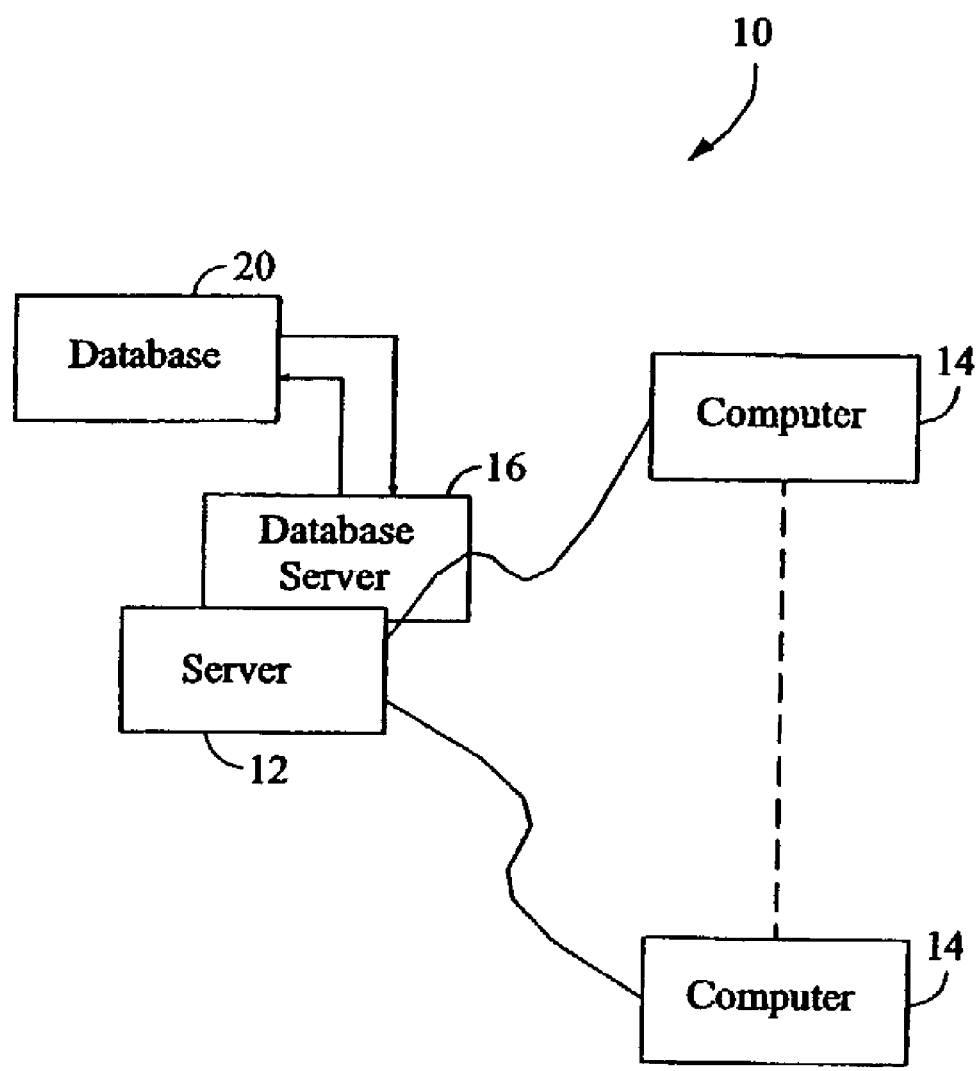
FIG. 1 is a simplified block diagram of a Clinical Research Coordination System (CRCS) in accordance with one embodiment of the present invention.

Example embodiments of systems and processes that facilitate integrated network-based electronic reporting and workflow process management related to a Clinical Research Coordination System (CRCS) are described below in detail. The systems and processes facilitate, for example, electronic submission of information using a client system, automated extraction of information, and web-based reporting for internal and external system users. The CRCS permits a clinical research entity to collect, manage, store, and provide clinical study data to authorized internal users and authorized outside users to facilitate medical diagnoses, optimize the use of medical equipment in the diagnoses and treatment of patients, and facilitate the production of next generation medical equipment and the optimization of clinical applications.

In the example embodiment, the CRCS is utilized to collect, track, display, and disseminate real time information regarding Clinical Study (CS) data for a clinical research entity. CS data includes at least one of a patient name, a patient sex, a patient medical history, a patient weight, a patient height, a patient age, a patient ID number, a modality of treatment and/or diagnosis, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of a patient within a specific clinical study conducted by the clinical research entity. In addition, the CRCS utilizes a plurality of standardized templates for inputting CS data for a clinical study. The CRCS also enables a user to track and analyze CS data to develop future generation product specifications and to optimize clinical applications. The CRCS further enables an authorized outside user to view, analyze, and comment on CS data. Additionally, the CRCS enables a supervisor to manage at least one clinical study. The CRCS also permits an authorized user for a clinical research entity to input CS data for a clinical study, edit CS data for an existing clinical study, review other user's comments and findings, and generate reports.

CS data is received by the CRCS which stores the CS data in a database, updates the database with CS data received, tracks the CS data received, provides CS data in response to an inquiry, allows an authorized outside user to review and comment on CS data, and provides a report to at least one user within the clinical research entity relating to the review of CS data by the authorized outside user.

In the CRCS, CS data is stored in the database. The network based CRCS provides convenient access to CS data including at least one of a patient name, a patient sex, a patient medical history, a patient weight, a patient height, a patient age, a patient ID number, a modality of treatment, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of a patient within a specific clinical study. A user must be authorized to gain access into the CRCS. In the example embodiment, the user logs onto CRCS. Once the CRCS home page is accessed, the user will be able to choose from a list of clinical studies that the user has been given access to view CS data. In an example embodiment, only an authorized user can access the CS data.

In one embodiment, a computer program is provided, and the program is embodied on a computer readable medium and utilizes a Structured Query Language (SQL), with a client user interface front-end for administration and a web interface for standard user input and reports. In an example embodiment, the system is web enabled and is run on a business-entity intranet. In yet another embodiment, the system is fully accessed by individuals having an authorized access outside the firewall of the business-entity through the Internet. In a further example embodiment, the system is being run in a Windows® environment (Windows is a registered trademark of Microsoft Corporation, Redmond, Wash.). The application is flexible and designed to run in various different environments without compromising any major functionality.

The systems and processes are not limited to the specific embodiments described herein. In addition, components of each system and each process can be practiced independent and separate from other components and processes described herein. Each component and process also can be used in combination with other assembly packages and processes.

FIG. 1 is a simplified block diagram of a Clinical Research Coordination System (CRCS) 10 including a server system 12, and a plurality of client sub-systems, also referred to as client systems 14, connected to server system 12. In one embodiment, client systems 14 are computers including a web browser, such that server system 12 is accessible to client systems 14 via the Internet. Client systems 14 are interconnected to the Internet through many interfaces including a network, such as a local area network (LAN) or a wide area network (WAN), dial-in-connections, cable modems and special high-speed ISDN lines. Client systems 14 could be any device capable of interconnecting to the Internet including a web-based phone, personal digital assistant (PDA), or other web-based connectable equipment. A database server 16 is connected to a database 20 containing information on a variety of matters, as described below in greater detail. In one embodiment, centralized database 20 is stored on server system 12 and can be accessed by potential users at one of client systems 14 by logging onto server system 12 through one of client systems 14. In an alternative embodiment database 20 is stored remotely from server system 12 and may be non-centralized.

Figure 2:
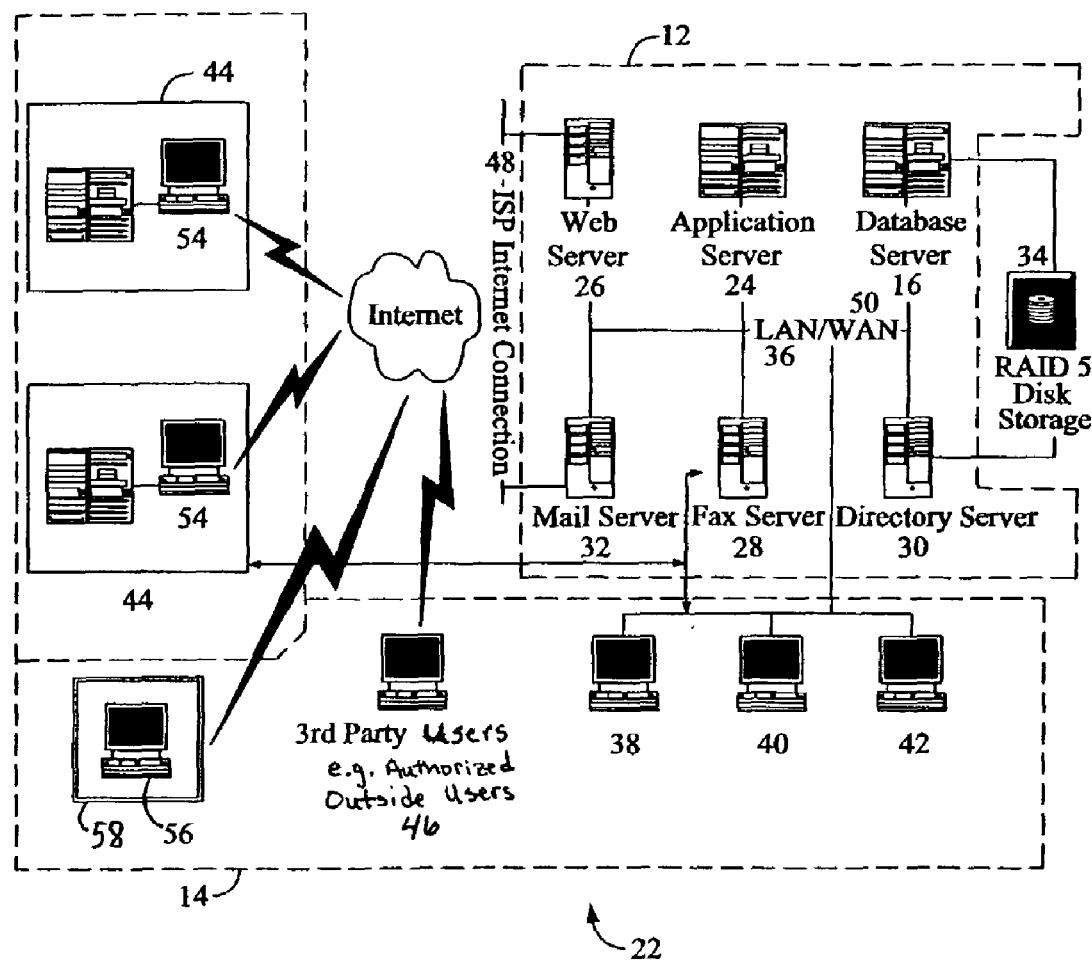
FIG. 2 is an expanded version block diagram of an example embodiment of a server architecture of the CRCS.

FIG. 2 is an expanded block diagram of an example embodiment of a server architecture of a CRCS 22. Components in system 22, identical to components of system 10 (shown in FIG. 1), are identified in FIG. 2 using the same reference numerals as used in FIG. 1. System 22 includes server system 12 and client systems 14. Server system 12 further includes database server 16, an application server 24, a web server 26, a fax server 28, a directory server 30, and a mail server 32. A disk storage unit 34 is coupled to database server 16 and directory server 30. Servers, 16, 24, 26, 28, 30, and 32 are coupled in a local area network (LAN) 36. In addition, a system administrator's workstation 38, a user workstation 40, and a supervisor's workstation 42 are coupled to LAN 36. Alternatively, workstations 38, 40, and 42 are coupled to LAN 36 via an Internet link or are connected through an Intranet.

Each workstation, 38, 40, and 42 is a personal computer having a web browser. Although the functions performed at the workstations typically are illustrated as being performed at respective workstations 38, 40, and 42, such functions can be performed at one of many personal computers coupled to LAN 36. Workstations 38, 40, and 42 are illustrated as being associated with separate functions only to facilitate an understanding of the different types of functions that can be performed by individuals having access to LAN 36. In an example embodiment, client system 14 includes workstation 40 which can be used by an authorized employee of the clinical research entity to review, manage, and comment on CS data.

Server system 12 is configured to be communicatively coupled to various individuals, including clinical research entity employees 44 and other third-party users, e.g., authorized outside users, 46 via an ISP Internet connection 48. The communication in the example embodiment is illustrated as being performed via the Internet, however, any other wide area network (WAN) type communication can be utilized in other embodiments, i.e., the systems and processes are not limited to being practiced via the Internet. In addition, and rather than WAN 50, local area network 36 could be used in place of WAN 50.

In the example embodiment, any authorized individual having a workstation 54 can access CRCS 22. At least one of the client systems includes a supervisor workstation 56 located at a remote location. Workstations 54 and 56 are personal computers having a web browser. Also, workstations 54 and 56 are configured to communicate with server system 12. Furthermore, fax server 28 communicates with remotely located client systems, including a client system 56 via a telephone link. Fax server 28 is configured to communicate with other client systems 38, 40, and 42 as well.

In one embodiment, a supervisor utilizing supervisor workstation 56 may access and manage a plurality of different clinical studies that may be stored in CRCS 22. The supervisor may extract CS data from the plurality of clinical studies to conduct data mining. Data mining includes comparing and contrasting CS data to determine whether trends exist with respect to the data. The supervisor may also control access to CRCS 22 and define who has permission to create and participate in clinical studies. Supervisor workstation 56 also enables the supervisor to track at least one of available memory on disk storage unit 34, common resources, network connections, and lists of common template values. In one embodiment, the supervisory control can be realized as a set of Java® servlets, a C++ computer program, or a C computer program (Java is a registered trademark of Sun Microsystems, Inc., Mountain View, Calif.). In another embodiment, each standardized template is in an eMatrix® format (eMatrix is a registered trademark of MatrixOne, Inc. Chelmsford, Mass.).

In one embodiment, supervisor workstation 56 also enables the supervisor to create a plurality of standardized templates stored in database 20 within CRCS 22. The plurality of standardized templates are used for inputting CS data for a clinical study. In one embodiment, each of the plurality of standardized templates may be reconfigured by the supervisor to prompt a user to enter a variety of information as needed for a specific clinical study.

In the example embodiment, workstation 56 is configured as an operational interface with medical imaging equipment 58. Medical equipment 58 may include, for example, but not limited to, a computed tomography, radiography, positron emission tomography, or ultrasound imaging device. Workstation 56 allows specific protocols of equipment operation to be actuated. Medical data is generated as part of the operation of these devices with a selected protocol, including diagnostic images, in the usual course of a clinical study. The medical data is automatically entered as part of the CS data by virtue of the communication of workstation 56 within CRCS 22. Furthermore, the CS data may include specific protocols for equipment operation used to generate the medical data. The medical data can later facilitate an efficacy evaluation of particular protocols for medical diagnosis. This type of evaluation is an output of a clinical study that facilitates the development of improved protocols and medical equipment.

Figure 3:
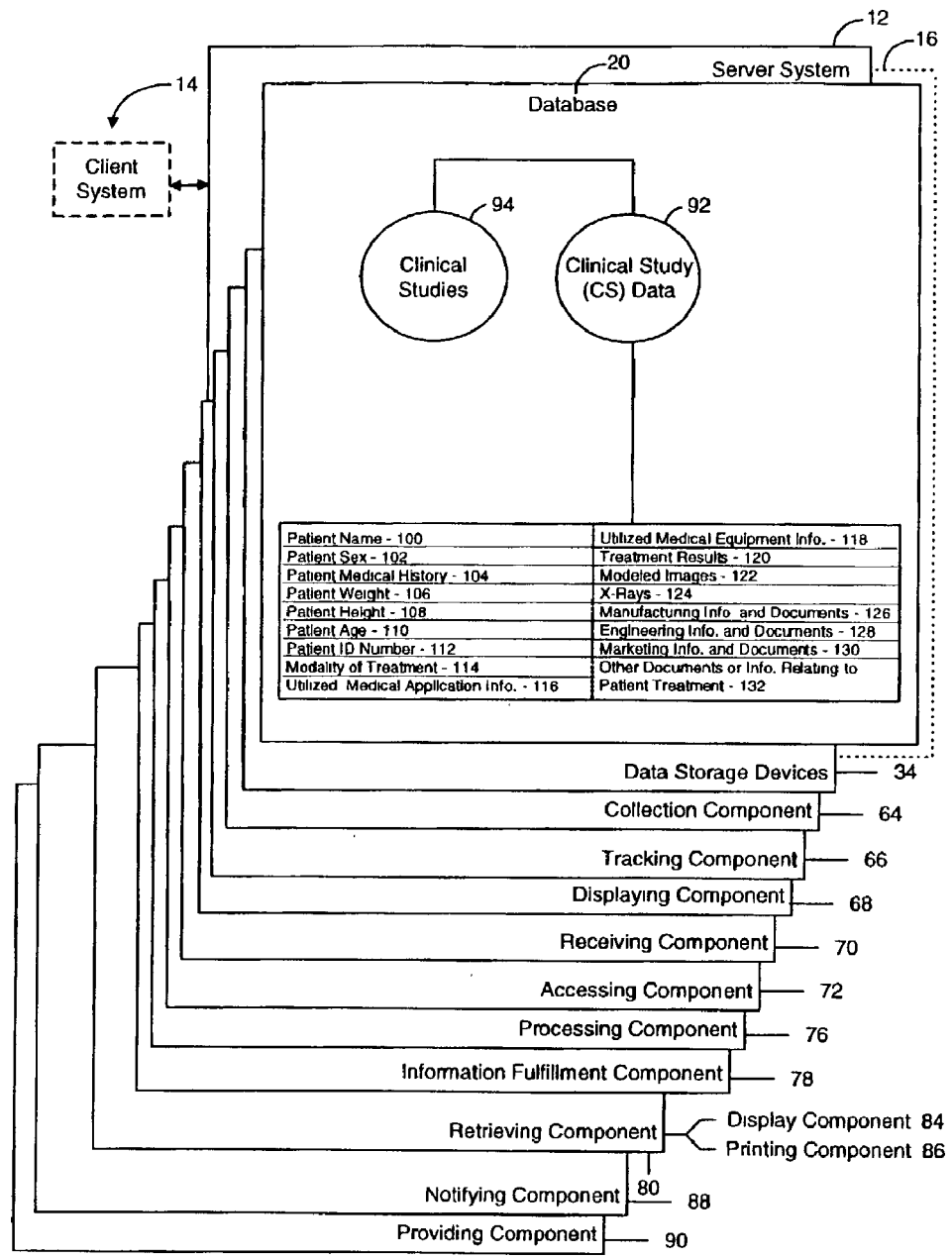
FIG. 3 illustrates an example configuration of a database within the database server of the server system including other related server components.

FIG. 3 illustrates an example configuration of database 20 within database server 16 of server system 12 shown in FIG. 1. Database 20 is coupled to several separate computer software components within server system 12 which perform specific tasks. In the example embodiment, server system 12 includes a collection component 64 for collecting data from users in database 20, a tracking component 66 for tracking data, and a displaying component 68 to display information. Tracking component 66 tracks and cross-references data, including modifying existing data.

Server system 12 also includes a receiving component 70 to receive a specific query from client system 14, and an accessing component 72 to access database 20 within data storage device 34. Receiving component 70 is programmed to receive a query from one of a plurality of users. Server system 12 further includes a processing component 76 for searching and processing received queries against database 20 containing a variety of information collected by collection component 64. An information fulfillment component 78, located in server system 12, enables the requested information to be downloaded to the plurality of users in response to the requests received by receiving component 70. Information fulfillment component 78 downloads the information after the information is retrieved from database 20 by a retrieving component 80. Retrieving component 80 retrieves, downloads and sends information to client system 14 based on a query received from client system 14.

Retrieving component 80 also includes a display component 84 that is configured to download information to be displayed on a client system's graphical user interface and a printing component 86 that is configured to print information. Retrieving component 80 generates reports requested by the user through client system 14 in a pre-determined format. System 10 is flexible to provide other alternative types of reports and is not constrained to the options set forth above.

Server system 12 also includes a notifying component 88 and a providing component 90. Notifying component 88 electronically transmits a message to client system 14 based on information inputted into server system 12, notifying a supervisor of a review of CS data by an authorized user, including the user's comments and findings. Providing component 90 electronically provides a report to supervisor workstation 56 (shown in FIG. 2) summarizing the review of the CS data by the authorized user, including the user's comments and findings.

In one embodiment, collection component 64, tracking component 66, displaying component 68, receiving component 70, processing component 76, information fulfillment component 78, retrieving component 80, display component 84, printing component 86, notifying component 88, and providing component 90 are computer programs embodied on computer readable medium.

Database 20 stores CS data 92 for each clinical study 94 conducted by the clinical research entity. CS data 92 includes at least one of a patient name 100, a patient sex 102, a patient medical history 104, a patient weight 106, a patient height 108, a patient age 110, a patient ID number 112, a modality of treatment 114, utilized medical application information 116, utilized medical equipment information 118, treatment results 120, modeled images 122, x-rays 124, manufacturing information and documents relating to utilized medical equipment 126, engineering information and documents relating to utilized medical equipment 128, marketing information and documents relating to utilized medical equipment 130, and any other documents or information 132 relating to the treatment of a patient within a specific clinical study conducted by the clinical research entity.

Utilized medical application information 116 and utilized medical equipment information 118 includes, but is not limited to, protocols utilized in medical applications and for operating medical equipment while treating a patient. For example, a protocol for a computed tomographic (CT) imaging system includes at least one of Gantry Speed, Helical Pitch, Collimation, Helical, Axial, and Cine. The protocols enable a physician or a technician conducting a specific medical application or operating a specific piece of medical equipment, in the example a CT imaging system, to correctly conduct the application or operate the piece of equipment when treating a patient. Other protocols for other applications and other equipment may also be inputted and utilized by CRCS 10.

CRCS 10 is utilized to collect, track, display, and disseminate real time information regarding CS data for a clinical research entity. In one embodiment, CRCS 10 utilizes a plurality of standardized templates for inputting CS data 92 for a clinical study. CRCS 10 also utilizes the plurality of standardized templates to display CS data 92 on client system 14. In one embodiment, each standardized template is in a Java® format, a C++ computer program format, or a C computer program format. In another embodiment, each standardized template is in an eMatrix® format (eMatrix is a registered trademark of MatrixOne, Inc. Chelmsford, Mass.). Each standardized template contains fields that prompt a user to enter specific CS data 92 or displays specific CS data 92 for a user to view and analyze. These fields may also capture and display workflow for a specific clinical study.

In one embodiment, when a user creates a new clinical study, the user selects a create a new clinical study button within system 10. System 10 then displays a standardized template wherein all the fields within the template are available for use. Additionally, specific fields common to many clinical studies can be selected from a drop down list, check boxes, or other manner for entering data could be used. Data is then entered by a user in other fields within the standardized template. In another embodiment, certain fields within a standardized template may be automatically filled based on the type of medical application or type of treatment being utilized to treat a patient.

In one embodiment, the standardized template function is realized as a Java® servlet. For example, when a user creates a new clinical study, the user utilizes a web browser on client system 14 to request a web page from the URL of the servlet. Upon receiving the request, the servlet checks the relevant authorization of the user and, if allowed, creates an instance of the requested standard template within its own memory space and also requests that the appropriate memory be allocated on database 20. The servlet then sends a web page back to the user displayed on client system 14 to prompt the user to enter the necessary CS data 92 through the fields on the requested standardized template. As new patients are added to the clinical study, CS data 92 relating to these new patients are entered through the fields on the standardized template generated by the servlet.

System 10 accumulates a variety of confidential data and has different access levels to control and monitor the security of and access to system 10. Authorization for access is assigned by system administrators on a need to know basis. In one embodiment, access is provided based on job functions. In yet another embodiment, system 10 provides access based on business-entity. The administration/editing capabilities within system 10 are also restricted to ensure that only authorized individuals have access to modify or edit the data existing in the system. System 10 manages and controls access to system data and information.

In another embodiment, system 10 enables a user to export CS data 92 to a computer program, for example, an Excel™ spreadsheet, such that the user can further analyze, review, and present the data. (Excel is a trademark of Microsoft Corporation, Redmond, Wash.) In another embodiment, system 10 enables a user to link certain documents and information to a patient involved in a clinical study. For example, a user may link to a specific patient involved in a clinical study at least one of a patient medical history, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents and information relating to the treatment and/or diagnosis of the patient. System 10 can then display these documents and information.

The architectures of system 10 as well as various components of system 10 are example only. Other architectures are possible and can be utilized in connection with practicing the processes described below.

Figure 4:
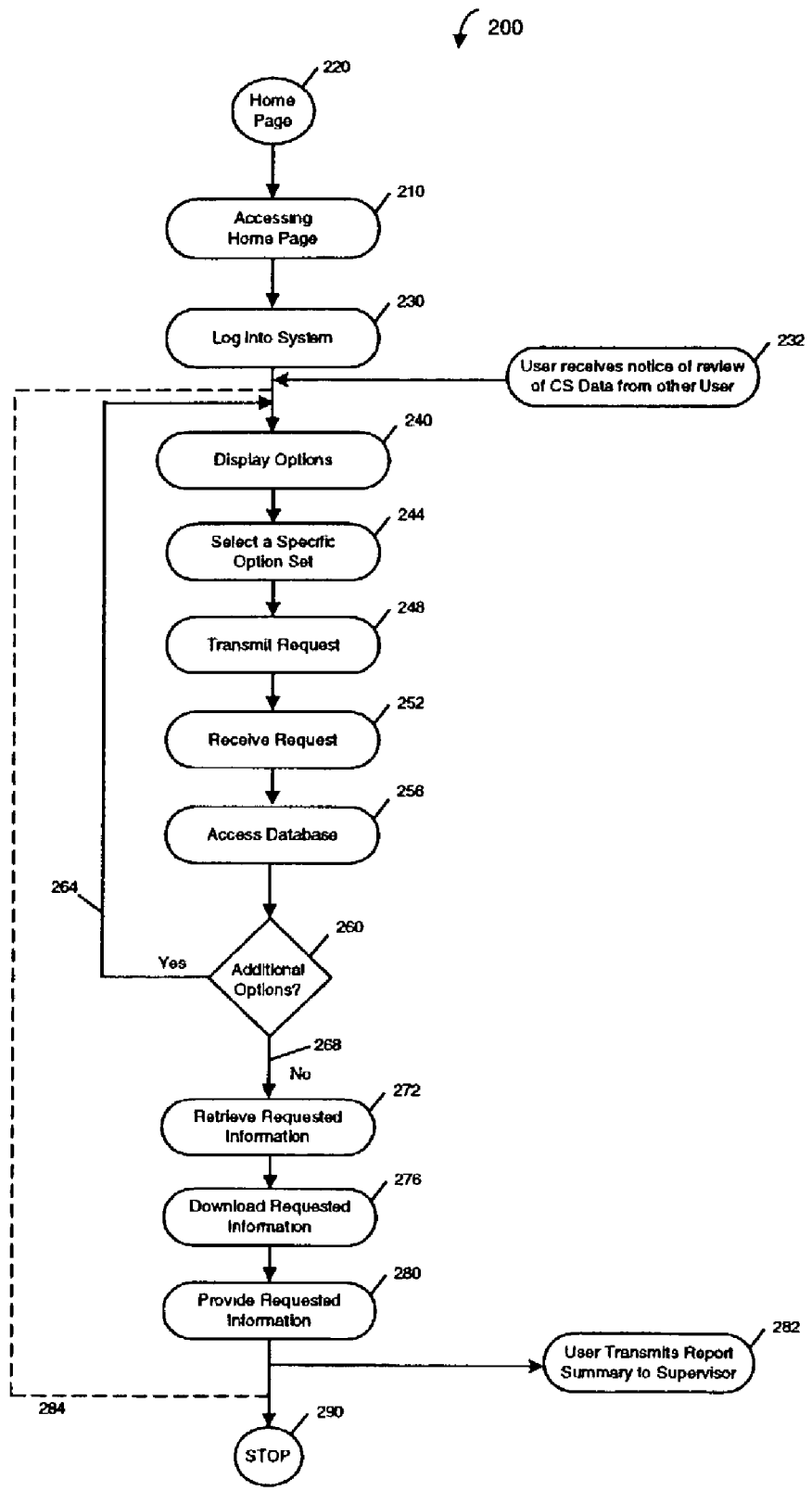
FIG. 4 is a flowchart illustrating example processes utilized by a CRCS.

FIG. 4 is a flowchart 200 illustrating example processes utilized by system 10. Initially, a user accesses 210 a user interface, such as a home page 220, of the web site through client system 14 (shown in FIG. 1). In one embodiment, client system 14, as well as server system 12, are protected from access by unauthorized individuals. The user logs-in 230 to system 10 using a password (not shown) or an employee payroll number for security. In the example embodiment, client system 14 is configured to receive 232 an electronic notice indicating to a user that a review of CS data by another user has occurred and any comments or findings relating to the review.

Client system 14 displays 240 options available to the user through links, check boxes, or pull-down lists. Once the user selects 244 an option (in one embodiment, relating to a specific clinical study being performed by the clinical research entity) from the available links, the request is transmitted 248 to server system 12. Transmitting 248 the request is accomplished, in one embodiment, either by click of a mouse or by a voice command. Once server system 12 (shown in FIG. 1) receives 252 the request, server system 12 accesses 256 database 20 (shown in FIG. 1). System 10 determines 260 if additional narrowing options are available. In one embodiment, additional narrowing options include at least one of clinical study name, clinical site, modality of treatment, protocol, and exam number selection pull-down lists and data fields. If additional narrowing options are available 264, system 10 displays 240 the options relating to the prior option selected by the user on client system 14. The user selects 244 the desired option and transmits the request 248. Server system 12 receives the request 252 and accesses 256 database 20. When system 10 determines that additional options 260 are not available 268, system 10 retrieves 272 requested information from database 20. The requested information is downloaded 276 and provided 280 to client system 14 from server 12. Client system 14 transmits a report 282, from a user to supervisor workstation 56 (shown in FIG. 2), which summarizes the user's review of the CS data, and includes the user's comments and findings. The user may continue to search 284 database 20 for other information or exit 290 from system 10.

CRCS 10 therefore permits a clinical research entity to collect, manage, store, and provide clinical study data to authorized internal users and authorized outside users to facilitate medical diagnoses, optimize the use of medical equipment in the diagnoses and treatment of patients, and facilitate the production of next generation medical equipment and the optimization of clinical applications. More specifically, CRCS 10 is utilized to collect, track, display, and disseminate real time information regarding CS data for a clinical research entity. CS data includes at least one of a patient name, a patient sex, a patient medical history, a patient weight, a patient height, a patient age, a patient ID number, a modality of treatment, utilized medical application information, utilized medical equipment information, treatment results, modeled images, x-rays, manufacturing information and documents relating to utilized medical equipment, engineering information and documents relating to utilized medical equipment, marketing information and documents relating to utilized medical equipment, and any other documents or information relating to the treatment of a patient within a specific clinical study conducted by the clinical research entity. In addition, CRCS 10 utilizes standardized templates for inputting CS data for a clinical study. CRCS 10 also enables a user to track and analyze CS data to develop future generation product specifications and to optimize clinical applications. CRCS 10 further enables an authorized outside user to view, analyze, and comment on CS data. Additionally, CRCS 10 enables a supervisor to manage at least one clinical study. CRCS 10 also permits an authorized user for a clinical research entity to input CS data for a clinical study, edit CS data for an existing clinical study, review other user's comments and findings, and generate reports. By enabling a clinical study entity to better manage CS data, CRCS 10 facilitates reducing transaction costs for the clinical study entity and facilitates reducing the amount of time spent on each clinical study by the clinical study entity.

While the invention has been described in terms of various specific embodiments, those skilled in the art will recognize that the invention can be practiced with modification within the spirit and scope of the claims.

The invention claimed is:

1. A method for managing clinical study (CS) information for a clinical research entity via a server computer coupled to a centralized database and at least one client computer, said method comprising:
    receiving at the server computer CS information relating to at least one patient involved in a clinical study, the CS information being entered through a user selected template displayed on the client computer, wherein the user selected template is selected from a plurality of templates stored in a centralized database, each of the plurality of templates configured to correspond to specific clinical studies;
    storing CS information received at the server computer in the centralized database;
    tracking CS information stared in the centralized database;
    updating the centralized database periodically with newly received information to maintain CS information; and
    providing CS information in response to an inquiry.

2. A method in accordance with claim 1 further comprising providing at least one medical device in communication with the at least one client computer, the at least one medical device includes at least one of a computed tomography device, a radiography device, a positron emission tomography device, and an ultrasound imaging device.

3. A method in accordance with claim 2 wherein receiving CS information comprises:
    using a template selected by a user from the plurality of templates stored in the centralized database to gather protocols for operating the at least one medical device;
    displaying the template on the client computer;
    operating the at least one medical device based on the entered protocols; and
    receiving at the server computer information generated as part of the operation of the at least one medical device including at least one of x-rays and diagnostic images for a patient involved in a clinical study.

4. A method in accordance with claim 1 further comprising transmitting from the server computer to the at least one client computer at least one report summarizing information and findings for a clinical study.

5. A method in accordance with claim 1 further comprising transmitting from the server computer to the at least one client computer at least one report summarizing CS information and findings for at least one patient involved in a clinical study.

6. A method in accordance with claim 1 wherein receiving CS information comprises:
    using a template selected by a user from the plurality of templates stored within the centralized database to gather CS information;
    displaying the selected template on the client computer; and
    inputting into the selected template at least one of a patient name, a patient sex, a patient medical history, a patient weight, a patient height, a patient age, a patient ID number, a modality of treatment and/or diagnosis, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents and information relating to the treatment and/or diagnosis patient involved in a clinical study conducted by the clinical research entity.

7. A method in accordance with claim 1 wherein tracking CS information comprises:
compiling a data report including at least one of a patient name, a patient sex, a patient medical history, a patient weight, a patient height, a patient age, a patient ID number, a modality of treatment and/or diagnosis, utilized medical application information, utilized medical equipment information, treatment and/or diagnosis results, modeled images, x-rays, manufacturing information relating to utilized medical equipment, engineering information relating to utilized medical equipment, marketing information relating to utilized medical equipment, and any other information relating to the treatment and/or diagnosis of a patient involved in a clinical study, conducted by the clinical research entity; and
transmitting the data report to a predesignated party at the at least one client computer.

8. A method in accordance with claim 1 wherein tracking CS information comprises exporting CS information selected by a user to at least one computer program.

9. A method in accordance with claim 1 wherein tracking CS information further comprises:
linking to a specific patient involved in a clinical study at least one of a patient medical history, utilized medical application information, utilized medical equipment information, treatment diagnosis results, modeled images, x-rays, manufacturing information and documents relating to utilized medical equipment, engineering information and documents relating to utilized medical equipment, marketing information and documents relating to utilized medical equipment, and any other documents and information relating to the treatment and/or diagnosis of the patient; and
displaying on the client computer at least one of the patient medical history, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of the patient.

10. A method in accordance with claim 1 wherein providing CS information comprises:
displaying on the client computer at least one of a list of patients involved in a clinical study and a list of clinical studies conducted by the clinical research entity;
receiving an inquiry from the client computer regarding at least one of a patient included within the patient list and a clinical study included within the clinical study list.

11. A method in accordance with claim 1 wherein providing CS information comprises:
receiving an inquiry from the client computer regarding at least one of a patient name, a patient sex, a patient medical history, a patient weight, a patient height, a patient age, a patient ID number, a modality of treatment diagnosis, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of a patient involved in a clinical study conducted by the clinical research entity; and
displaying information on the client computer regarding at least one of the patient name, the patient sex, the patient medical history, the patient weight, the patient height, the patient age, the patient ID number, the modality of treatment diagnosis, utilized medical application information, utilized medical equipment information, treatment diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of the patient.

12. A method in accordance with claim 1 wherein providing CS information comprises:
accessing the centralized database;
searching the database regarding the specific inquiry;
retrieving information from the database; and
transmitting the retrieved information to the client computer for display by the client computer.

13. A method in accordance with claim 1 further comprising connecting the client computer and the server computer via a network that includes one of a wide area network, a local area network, an intranet and the Internet.

14. A method tor managing clinical study (CS) information for a clinical research entity via a server computer coupled to a centralized database and at least one client computer, the at least one client computer in communication with at least one medical device, said method comprising:
using a template selected by a user from a plurality of templates stored in a centralized database to gather protocols for acquisition of image data via the at least one medical device, each of the plurality of templates configured to correspond to specific clinical studies;
operating the at least one medical device for acquiring image data based on the entered protocols;
receiving at the server computer CS information that relates to at least one patient involved in a clinical study, the CS information being entered through the user selected template displayed on the client computer and being generated as part of the operation of the at least one medical device including acquisition of diagnostic images;
storing CS information received at the server computer in the centralized database;
tracking CS information stored in the centralized database;
updating the centralized database periodically with newly received CS information to maintain CS information;
providing CS information in response to an inquiry; and
transmitting from the server computer to the at least one client computer at least one report relating to CS information and findings for at least one of a clinical study and a patient involved in a clinical study.

15. A method in accordance with claim 14 further comprising providing at least one medical device including at least one of a computed tomography device, a radiography device, a positron emission tomography device, and an ultrasound imaging device.

16. A method in accordance with claim 14 wherein receiving CS information comprises:
receiving at the server computer at least one of a patient name, a patient sex, a patient medical history, a patient weight, a patient height, a patient age, a patient ID number, a modality of treatment and/or diagnosis, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of a patient involved in a clinical study conducted by the clinical research entity.

17. A network based system for managing clinical study (CS) information, said system comprising:
a client computer comprising a browser;
a centralized database, stored on a tangible computer-readable medium, for storing information and a plurality of templates; and
a server computer configured to be coupled to said client computer and said database, said server computer further configured to:
receive CS information relating to at least one patient involved in a clinical study, said CS information being entered through a user selected template displayed on said client computer, wherein the user selected template is selected from the plurality of templates stored in the centralized database, each of the plurality of templates configured to correspond to specific clinical studies;
store CS information in said centralized database;
track CS information;
update said centralized database periodically with newly received CS information to maintain CS information; and
provide CS information in response to an inquiry by a user.

18. A system in accordance with claim 17 further comprising at least one medical device in communication with said client computer and said server computer, said at least one medical device including at least one of a computed tomography device, a radiography device, a positron emission tomography device, and an ultrasound imaging device.

19. A system in accordance with claim 18 wherein said server computer further comprises a receiving component that:
uses a template selected by a user from said plurality of templates stored in said centralized database to gather protocols for operating said at least one medical device;
displays said selected template on said client computer;
operates said at least one medical device based on said entered protocols; and
receives CS information generated as part of the operation of said at least one medical device including at least one of x-rays and diagnostic images for a patient involved in a clinical study.

20. A system in accordance with claim 17 wherein said server computer is further configured to transmit to said client computer at least one report summarizing CS information and findings for a clinical study.

21. A system in accordance with claim 17 wherein said server computer is further configured to transmit to said client computer at least one report summarizing CS information and findings for at least one patient involved in a clinical study.

22. A system in accordance with claim 17 wherein said server computer further comprises a receiving component that:
uses a template selected by a user from said plurality of templates stored in said centralized database to gather CS information;
displays said selected template on said client computer; and
receives through said selected template at least one of a patient name, a patient sex, a patient medical history, a patient weight, a patient height, a patient-age, a patient ID number, a modality of treatment and/or diagnosis, utilized medical application, information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents and information relating to the treatment and/or diagnosis of a patient involved in a clinical study conducted by the clinical research entity.

23. A system in accordance with claim 17 wherein said server computer further comprises a tracking component that;
compiles a data report including at least one of a patient name, a patient sex, a patient medical history, a patient weight, a patient height, a patient age, a patient ID number, a modality of treatment and/or diagnosis, utilized medical application information, utilized medical equipment information, treatment and/or diagnosis results, modeled images, x-rays, manufacturing information relating to utilized medical equipment, engineering information relating to utilized medical equipment, marketing information relating to utilized medical equipment, and any other information relating to the treatment and/or diagnosis of a patient involved in a clinical study conducted by the clinical research entity; and
transmits said data report to a predesignated party at said client computer.

24. A system in accordance with claim 17 wherein said server computer further comprises a tracking component that exports CS information selected by a user to at least one computer program.

25. A system in accordance with claim 17 wherein said server computer further comprises a tracking component that;
links to a specific patient involved in a clinical study at least one of a patient medical history, utilized medical application-information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents and information relating to the treatment and/or diagnosis of said patient; and
displays on said client computer at least one of said patient medical history, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of said patient.

26. A system in accordance with claim 17 wherein said server computer further comprises a providing component that:
displays on said client computer at least one of a list of patients involved in a clinical study and a list of clinical studies conducted by the clinical research entity; and
receives an inquiry from said client computer regarding at least one of a patient included within said patient list and a clinical study included within said clinical study list.

27. A system in accordance with claim 17 wherein said server computer further comprises a providing component that:
receives an inquiry from said client computer regarding at least one of a patient name, a patient sex, a patient medical history, a patient weight, a patient height, a patient age, a patient ID number, a modality of treatment and/or diagnosis, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of a patient involved in a clinical study conducted by the clinical research entity; and
displays information on said client computer regarding at least one of said patient name, said patient sex, said patient medical history, said patient weight, said patient height, said patient age, said patient ID number, said modality of treatment and/or diagnosis, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of said patient.

28. A system in accordance with claim 17 wherein said server computer further comprises a providing component that:
accesses said centralized database;
searches said database regarding a specific inquiry;
retrieves information from said database; and
transmits said retrieved information to said client computer for display by said client system computer.

29. A system in accordance with claim 17 wherein said server computer, said client computer, and said database we connected via a network that includes one of a wide area network, a local area network, an intranet and the Internet.

30. A network based system for managing clinical study (CS) information, said system comprising:
a client computer comprising a browser;
at least one medical device in communication with said client computer;
a centralized database, stored on a tangible computer-readable medium, for storing information and a plurality of templates; and
a server computer configured to he coupled to said client computer and said database, said server computer further configured to:
use a template selected by a user from the plurality of templates stored in the centralized database to gather protocols for acquisition of image data via the at least one medical device, each of the plurality of templates configured to correspond to specific clinical studies;
operate said at least one medical device for acquiring image data based on said entered protocols;
receive CS information relating to at least one patient involved in a clinical study, said CS information entered through a user selected template displayed on said client computer and generated as part of the operation of said at least one medical device including acquisition of diagnostic images;
store CS information in said centralized database;
track CS information;
update said centralized database periodically with newly received CS information to maintain CS information;
provide CS information in response to an inquiry; and
transmit to said client computer at least one report relating to CS information and findings for at least one of a clinical study and a patient involved in a clinical study.

31. A system in accordance with claim 30 wherein said at least one medical device comprises at least one of a computed tomography device, a radiography device, a positron emission tomography device, and an ultrasound imaging device.

32. A system in accordance with claim 30 wherein said server commuter further comprises a receiving component that:
receives at least one of a patient name, a patient sex, a patient medical history, a patient weight, a patient height, a patient age, a patient ID number, a modality of treatment and/or diagnosis, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of a patient involved in a clinical study conducted by the clinical research entity.

33. A computer program embodied on a non-transitory computer readable medium for managing clinical study (CS) information, said program comprising a code segment that;
receives CS information relating to at least one patient involved in a clinical study through a user selected template displayed on a client computer, wherein the user selected template is selected from a plurality of templates stored in a centralized database, each of the plurality of templates configured to correspond to specific clinical studies;
maintains a database by adding, deleting and updating CS information; tracks CS information;
provides CS information in response to an inquiry by a user; and
transmits to said client computer at least one report summarizing CS information and findings relating to at least one of a clinical study and a patient involved in a clinical study.

34. A computer program in accordance with claim 33 further comprising a code segment that enables at least one medical device to communicate with said client computer wherein said at least one medical device includes at least one of a computed tomography device, a radiography device, a positron emission tomography device, and an ultrasound imaging device.

35. A computer program in accordance claim 34 further comprising a code segment that:

displays a template selected by a user on said client computer;

uses said selected template to gather protocols for operating said at least one medical device;

operates said at least one medical device based on said entered protocols; and receives CS information generated as part of the operation of said at least one medical device including at least one of x-rays and diagnostic images.

36. A computer program in accordance with claim 33 further comprising a code segment that:

displays a template selected by a user on said client computer;

uses said selected template to gather US information; and receives through said selected template at least one of a patient name, a patient sex, a patient medical history, a patient weight, a patient height, a patient age, a patient ID number, a modality of treatment and/or diagnosis, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents and information relating to the treatment and/or diagnosis of a patient involved in a clinical study conducted by the clinical research entity.

37. A computer program in accordance with claim 33 further comprising a code segment that:

compiles a data report including at least one of a patient name, a patient sex, a patient medical history, a patient weight, a patient height, a patient age, a patient ID number, a modality of treatment and/or diagnosis, utilized medical application information, utilized medical equipment information, treatment and/or diagnosis results, modeled images, x-rays, manufacturing information relating to utilized medical equipment, engineering information relating to utilized medical equipment, marketing information relating to utilized medical equipment, and any other information relating to the treatment and/or diagnosis of a patient involved in a clinical study conducted by the clinical research entity; and transmits said data report to a predesignated party at said client computer.

38. A computer program in accordance with claim 33 further comprising a code segment that:

links to a specific patient involved in a clinical study at least one of a patient medical history, medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents and information relating to the treatment and/or diagnosis of said patient; and displays on said client computer at least one of said patient medical history, utilized medical application information, utilized medical equipment information, treatment and/or diagnosis results, modeled images, x-rays; manufacturing information and documents relating to utilized medical equipment, engineering information and documents relating to utilized medical equipment, marketing information and documents relating to utilized medical equipment, and any other documents or information relating to the treatment and/or diagnosis of said patient.

39. A computer program in accordance with claim 33 further comprising a code segment that:

displays on said client computer at least one of a list of patients involved in a clinical study and a list of clinical studies conducted by the clinical research entity; and receives an inquiry from said the client computer regarding at least one of a patient included within said patient list and a clinical study included within said clinical study list.

40. A computer program in accordance with claim 33 further comprising a code segment that:

receives an inquiry from said client computer regarding at least one of a patient name, a patient sex, a patient medical history, a patient weight, a patient height, a patient age, a patient ID number, a modality of treatment and/or diagnosis, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of the patient involved in a clinical study conducted by the clinical research entity; and displays information on said the client computer regarding at least one of said patient name, said patient sex, said patient medical history, said patient weight, said patient height, said patient age, said patient ID number, said modality of treatment and/or diagnosis, utilized medical application information, utilized medical equipment information, treatment and/or diagnosis results, modeled images, x-rays, manufacturing information and documents relating to utilized medical equipment, engineering information and documents relating to utilized medical equipment, marketing information and documents relating to utilized medical equipment, and any other documents or information relating to the treatment and/or diagnosis of said patient.

* * * * *

UNITED STATES PATENT AND TRADEMARK OFFICE
CERTIFICATE OF CORRECTION

PATENT NO. : 7,870,006 B2
APPLICATION NO. : 10/065159
DATED : January 11, 2011
INVENTOR(S) : Tkaczyk et al.

It is certified that error appears in the above-identified patent and that said Letters Patent is hereby corrected as shown below:

On the Face Page, in Field (56), under "OTHER PUBLICATIONS", in Column 2, Line 4, delete "ledalaw" and insert -- leda.law --, therefor.

In Column 4, Line 27, delete "(SQL)," and insert -- (SQL) --, therefor.

In Column 5, Line 10, delete "Servers," and insert -- Servers --, therefor.

In Column 10, Line 15, in Claim 1, delete "stared" and insert -- stored --, therefor.

In Column 11, Line 5, in Claim 7, delete "1D" and insert -- ID --, therefor.

In Column 11, Line 15, in Claim 7, delete "study," and insert -- study --, therefor.

In Column 12, Line 23, in Claim 12, delete "computer," and insert -- computer. --, therefor.

In Column 14, Line 9, in Claim 22, delete "patient-age," and insert -- patient age, --, therefor.

In Column 14, Line 11, in Claim 22, delete "application," and insert -- application --, therefor.

In Column 14, Line 23, in Claim 23, delete "that;" and insert -- that: --, therefor.

In Column 14, Line 46, in Claim 25, delete "that;" and insert -- that: --, therefor.

In Column 14, Lines 48-49, in Claim 25, delete "application-information," and insert -- application information, --, therefor.

In Column 15, Line 51, in Claim 29, delete "we" and insert -- are --, therefor.

In Column 15, Line 62, in Claim 30, delete "to he" and insert -- to be --, therefor.

Signed and Sealed this
Seventeenth Day of May, 2011

David J. Kappos
*Director of the United States Patent and Trademark Office*

CERTIFICATE OF CORRECTION (continued)
U.S. Pat. No. 7,870,006 B2

In Column 16, Line 43, in Claim 33, delete "that;" and insert -- that: --, therefor.

In Column 18, Line 8, in Claim 38, delete "x-rays;" and insert -- x-rays, --, therefor.